United States Patent
Yakimoski et al.

(10) Patent No.: US 7,593,101 B2
(45) Date of Patent: Sep. 22, 2009

(54) HIGH-PRESSURE CROSS-POLAR MICROSCOPY CELLS HAVING ADJUSTABLE FLUID PASSAGE AND METHODS OF USE

(75) Inventors: Todd Yakimoski, Beaumont (CA); Scott Jacobs, Edmonton (CA); Ken Sitko, Edmonton (CA); Ahmed Hammami, Edmonton (CA); Terry Sopkow, Edmonton (CA); Craig Borman, Camrose (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 272 days.

(21) Appl. No.: 11/733,573

(22) Filed: Apr. 10, 2007

(65) Prior Publication Data

US 2008/0252881 A1  Oct. 16, 2008

(51) Int. Cl.
*G01N 1/10* (2006.01)
*G01N 21/25* (2006.01)
*G01J 3/50* (2006.01)

(52) U.S. Cl. ............... 356/246; 356/244; 356/436; 356/413; 250/573

(58) Field of Classification Search ............ 356/244, 356/246, 432, 436–438, 413; 250/458.1, 250/461 R, 343, 373, 225, 227.11, 429, 573, 250/576
See application file for complete search history.

(56) References Cited

U.S. PATENT DOCUMENTS 5,003,174 A * 3/1991 Datwyler et al. ............ 250/343
5,223,716 A * 6/1993 Rossiter .................... 250/343
5,269,937 A * 12/1993 Dollinger et al. ........... 210/656
5,500,735 A * 3/1996 Bentley et al. ............. 356/364
5,905,271 A   5/1999 Wynn
5,949,536 A * 9/1999 Mark ....................... 356/246

(Continued)

FOREIGN PATENT DOCUMENTS

GB        2371858        4/2007

(Continued)

OTHER PUBLICATIONS

Karan, K., Ratulowski, J., Measurement of Waxy Crude Properties Using Novel Laboratory Techniques, SPE 62945 (2000), Society of Petroleum Engineers.

(Continued)

*Primary Examiner*—Sang Nguyen
(74) *Attorney, Agent, or Firm*—Jeffrey L. Wendt; Wayne I. Kanak

(57) ABSTRACT

Apparatus and methods are described for observing samples at non-ambient temperatures and pressures. One apparatus comprises a cell body having a fluid flow-through passage and a light passage intersecting the fluid flow-through passage at an adjustable light pathlength fluid analysis region; first and second light-transmissive windows in the light passage, each window having at least one crystal axis aligned longitudinally with a longitudinal axis of the window, the windows having opposed, spaced apart, substantially flat surfaces defining the adjustable light pathlength fluid analysis region, the first window having a first window holder and the second window having a second window holder, the first window rotationally isolated from the first window holder, the second window rotationally coupled to the second window holder, the first window holder able to gradually move the first window and thus adjust the light pathlength; and first and second light polarization filters.

20 Claims, 2 Drawing Sheets

U.S. PATENT DOCUMENTS

| | | | |
|---|---|---|---|
| 6,188,813 B1 * | 2/2001 | Dourdeville et al. | 385/12 |
| 6,307,204 B1 * | 10/2001 | Kanomata et al. | 250/373 |
| 6,501,072 B2 | 12/2002 | Mullins et al. | |
| 6,587,195 B1 | 7/2003 | Jennings | |
| 6,717,665 B2 * | 4/2004 | Wagner et al. | 356/244 |
| 6,997,055 B2 | 2/2006 | DiFoggio | |
| 7,075,652 B1 * | 7/2006 | Sarvazyan et al. | 356/432 |
| 7,079,242 B2 | 7/2006 | Bordelon | |
| 7,196,786 B2 | 3/2007 | DiFoggio | |
| 2003/0033866 A1 | 2/2003 | Diakonov et al. | |

FOREIGN PATENT DOCUMENTS

| | | |
|---|---|---|
| WO | 9820338 | 5/1998 |
| WO | 0237084 | 5/2002 |

OTHER PUBLICATIONS

Ratulowski et al., "Flow Assurance and Subsea Productivity: Closing the Loop with Connectivity and Measurements", SPE Paper 90244 (2004) Society of Petroleum Engineers Inc.

A. Hammami and J. Ratulowski: "Asphaltenes, Heavy Oils and Petroleomics, Oliver C. Mullins, Eric Y. Sheu, Ahmed Hammami, Alan Marshall, Editors, Kluwer Academic Publications, "Precipitation and Deposition of Aasphaltenes in Production Systems: A Flow Assurance Overview, Chapter 23, 2006.

M. Zougari, S. Jacobs, A. Hammami, G.Broze, M. Flannery. J. Ratulowski and A. Stankiewicz,"Novel Organic Solid Deposition and Control Device for Live Oils: Design and Applications", Energy & Fuels, 20 (2006), 1656-1663.

* cited by examiner

HIGH-PRESSURE CROSS-POLAR MICROSCOPY CELLS HAVING ADJUSTABLE FLUID PASSAGE AND METHODS OF USE

BACKGROUND OF THE INVENTION

1. Field of Invention

The present invention relates generally to the field of fluid analysis at temperature and pressure conditions existing at the source of the fluid, or at least temperatures different than ambient, including, but not limited to, reservoir hydrocarbon and aqueous based fluids, drilling muds, frac fluids, and the like having one or more phases (gases, solids and liquids).

2. Related Art

Fluid systems, under the influence of changes in one or more of pressure, temperature, fluid mixing, and/or chemical composition, may contain or develop solid particles that are of interest. One method of investigation uses visible light passing through a sample of the fluid to study the development and properties of these solid particles. There are equipment and experimental limitations to increasing the power of the light source, yet some fluid samples transmit less light than others; therefore it is desirable to be able to change the thickness of the fluid sample under investigation. Furthermore it is desirable to make this change while the sample remains at or near the pressure and temperature of interest.

U.S. Pat. No. 7,079,242, assigned to Core Laboratories, discloses a method and apparatus for determining characteristics of particles in a fluid sample. The method comprises passing light through a window in a view cell in order to observe particles of interest in a pressurized fluid. The operation of pumps causes a sample fluid to pass through the view cell, the view cell having ports connected to a chamber having windows positioned on either side of the chamber to allow visual examination of the sample fluid as it traverses through the chamber. The size of chamber may be adjustable to maintain a predetermined light transmission through the sample fluid as the properties of the fluid samples change. However, adjustment of the size of the sample chamber, either manually or hydraulically, requires rotating the cell windows. This is disadvantageous if one desires to study the fluid using polarized light, as the alignment of the crystal axes of the windows will change upon rotation.

U.S. Pat. No. 5,003,174, assigned to Bruker Analytische Messtechnik GmbH, discloses an optical high-pressure view cell that has stepped windows that are optimized for infrared spectroscopy. By giving the windows of the measuring cell according to the patent a stepped design it is possible to make the distance between surfaces defining the sample chamber as small as desired, by convenient selection of the dimensions of a central, cylindrical neck portion of the cell windows, making it possible to realize chambers with an extremely short light path required for certain measurements. This device, however, requires the cell to be disassembled and reassembled with windows of different central, cylindrical neck portion lengths in order to change the sample chamber size, which is inconvenient and time consuming, and does not discuss use of polarized light.

U.S. Pat. No. 5,905,271, assigned to Wedgewood Technology, discloses an inline optical sensor with vernier optical pathlength adjustment and photometric calibration, wherein the adjustable optical path intersects a flowing product stream. The disclosed device apparently permits the optical pathlength through the product stream to be adjusted with a degree of precision which is more than an order of magnitude greater than tolerances of previous inline optical sensors, and permits calibration standards to be inserted and removed without disturbing the pathlength of the optical system or degrading the signal from the system. While it appears the pathlength can be adjusted in this device without changing alignment of the windows, there is no discussion of use of polarized light or cross-polarization filters; only a spectral filter for light entering a detector, and calibration filter are discussed.

Karan and Ratulowski described visual measurement techniques and apparatus for visually measuring pour point and other properties of waxy crude oils at pressures up to 3000 psi[21 MPa]. Measurements of the live oil wax appearance temperature (WAT) were performed using a high pressure cross polar microscope and a laser-based solids detection system. Karan, K., Ratulowski, J., "Measurement of Waxy Crude Properties Using Novel Laboratory Techniques, SPE 62945 (2000), Society of Petroleum Engineers.

Ratulowski et al., "Flow Assurance and Subsea Productivity: Closing the Loop with Connectivity and Measurements", SPE Paper 90244 (2004) Society of Petroleum Engineers Inc., describe a dynamic approach to managing the risk of hydrocarbons flow interruptions, including the use of real-time measurements during production form the reservoir, the wellbore, and the subsea infrastructure, in monitoring and optimizing a hydrocarbon production system.

Asphaltenes are heavy, highly aromatic molecules that often precipitate from oils due to reductions in pressure and/or temperature or blending with incompatible fluids (see A. Hammami and J. Ratulowski in: Asphaltenes, Heavy Oils and Petroleomics, Oliver C. Mullins, Eric Y. Sheu, Ahmed Hammami, Alan Marshall, Editors, Kluwer Academic Publications, PRECIPITATION AND DEPOSITION OF ASPHALTENES IN PRODUCTION SYSTEMS: A FLOW ASSURANCE OVERVIEW, Chapter 23, 2006). Asphaktenes also contain multiple polar compounds, and may contain intramolecular species including oxygen, nitrogen, and sulfur, that may make the asphaltene molecules surface active. This surface activity may lead to asphaltene deposition on the walls of process equipment and transportation pipelines and allow asphaltene to participate in the stabilization of water-in-oil emulsions. The "strength" of the surface activity of individual asphaltene molecules is dependent on the variation in asphaltene composition. There is experimental evidence that a small, specific sub-fractions of the asphaltene is responsible for the deposits found on solid surfaces (see, for example, M. Zougari, S. Jacobs, A. Hammami, G. Broze, M. Flannery, J. Ratulowski and A. Stankiewicz, "Novel Organic Solid Deposition and Control Device for Live Oils: Design and Applications" Energy & Fuels, 20 (2006) 1656-1663).

Current experimental methods of studying asphaltenes in reservoir fluids involve the detection of solid precipitates in visual or non-visual pressure-volume-temperature (PVT) cells. A hydrocarbon-based fluid would be placed inside the PVT cell under pressure and temperature conditions similar to those experienced within a petroleum reservoir or in the petroleum production process. The pressure and/or temperature of the fluid would then be changed to induce the formation of a solid precipitate (e.g. asphaltene). Detection of solid formation in the hydrocarbon fluid may be done using near-infrared detectors, x-ray detection, or visual detection via a high pressure, high temperature microscopy method. The devices used in these detection methods are limited to suspended particle detection only and cannot change cell size, nor do they use polarized light for analysis (i.e. they can not distinguish between asphaltenes and waxes). They are also limited to fluids that are transparent enough to allow sufficient light to pass (i.e., they cannot be used with dark oils).

In the case of precipitated asphaltenes, high-temperature, high-pressure filtration may be used to collect the asphaltene aggregates and/or floes. While commonly used, the high-pressure, high-temperature filtration process contains some potentially serious limitations to the analysis of asphaltene precipitate. The first and obvious limitation is that the floc size and amount of the recovered asphaltene depends on the pore size of the filter. Also, one must be very careful not to cause precipitated solids (wax and/or asphaltenes) to grate through the pores of the filter by creating too large of a pressure drop across the filter. Secondly, asphaltenes collected by filtration often contain trapped oil that contains dissolved organic solids (wax or asphaltene). There is a risk that these dissolved solids, particularly asphaltenes, can be precipitated during the removal of the trapped oil. The solids from the trapped oil would then be carried through with the filtered asphaltene precipitate, thus representing a "contaminant" that can affect subsequent analytical characterization. Finally, any measurements completed on the filtered solids (e.g., asphaltene) will only provide information about "average" asphaltene properties. The current protocols do not permit sampling and analysis of individual floes and/or aggregates using adjustable pathlength cells and polarized light, an exercise that may reveal possible variations in chemical composition between the aggregates. With an adjustable pathlength, high-temperature, high-pressure cell and polarized light, it may be possible to detect these compositional variations that contribute to both the surface activity and aggregation behavior of asphaltenes.

A long, but heretofore unmet, need exists in the art for apparatus and methods for studying properties of a sample at temperatures and pressures representing those existing at the source of the sample, or at least different than ambient laboratory conditions, using an adjustable pathlength view cell and polarized light.

SUMMARY OF THE INVENTION

In accordance with the present invention, apparatus and methods for studying properties of a sample under temperature and pressure conditions representative of the source of the sample (or at least different from ambient conditions) using an adjustable pathlength view cell and polarized light are described. The temperature and pressure conditions of the sample may be those of a petroleum reservoir or other hydrocarbon-bearing geologic formation, but the invention is not so limited. The sample may be sub-ambient, ambient, or above-ambient in temperature and pressure, including, but not limited to compositions comprising hydrocarbons (including sour hydrocarbons which may include hydrogen sulfide, mercaptans, and other sulfur-containing compounds), water, organic and/or inorganic solids, and may include micelles, macromolecules, globules, resins, asphaltenes, wax crystals, hydrocarbon and aqueous based fluids, drilling muds, frac fluids, and the like having multiple phases (gaseous, solid and liquid). The sample composition may comprise one or more of each phase. Stated differently, a sample composition may comprise one or more liquid phases, one or more solid phases, and one or more gaseous phases. Apparatus of the invention may be used to distinguish and quantify (through particle size analysis) between wax and asphaltene precipitates, and may also be used for hydrate studies (i.e. temperatures down to −20° C. and lower).

In general terms, apparatus of the invention comprise a cell body, a fluid flow passage, and two window retention assemblies comprising two or more light-transmissive windows. A unique feature of apparatus of the invention is that the gap between the windows may be adjusted without changing the crystal alignment of the windows. One reason for having this capability is that fluid studies using the properties of polarized light may be run while adjusting the thickness of the fluid sample. Furthermore this gap adjustment may be done while the cell is pressurized. Apparatus within the invention are view cells intended for studying fluids at pressures up to and beyond 25,000 psi[172 MPa] over a wide temperature range while maintaining the ability to vary the thickness of the stationary or flowing fluid sample being studied.

One aspect of the invention are cell apparatus comprising:

(a) a cell body having a fluid flow-through passage and a light passage intersecting the fluid flow-through passage at an adjustable light pathlength fluid analysis region in the cell body, the cell body comprised of material capable of maintaining temperature and pressure in at least the fluid analysis region at least different than ambient conditions, and in certain embodiments representative of a hydrocarbon-bearing reservoir;

(b) first and second light-transmissive windows in the light passage, each window having at least one crystal axis aligned longitudinally with a longitudinal axis of the window, the windows having opposed, spaced apart, substantially flat surfaces defining the adjustable light pathlength fluid analysis region, each window having respective window holders, the first window rotationally isolated from its window holder, the second window rotationally coupled to its window holder, the first window holder able to gradually translate the first window and thus adjust the light pathlength (optionally, if sapphire is used for the windows, and cross-polarization filters are used, the a-axis is oriented); and (c) first and second light polarization filters positioned in the light passage, the first filter optionally positioned between a light entrance and the first window holder, the second filter optionally positioned in the light passage between a light exit and the second window holder.

Each window and window holder pair may be components of respective window retention assemblies, one window retention assembly comprising the first window, the first window holder, a first spacer between the first window and its window holder, and a roller bearing assembly between the spacer and the first window holder. The first window may have a first sleeve adhered thereto, the first sleeve may in turn be connected to its spacer via one or more dowel pins. A first seal assembly hydraulically seals the first window assembly and constrain fluid being tested to the fluid analysis region defined between the opposed, spaced apart, substantially flat surfaces of the first and second windows. This first window retention assembly allows the first window to be moved closer to or further away from the second window, thereby adjusting the distance between the opposed, substantially flat surfaces of the first and second windows, and therefore adjust the size of the fluid analysis region. Importantly, during this movement the first window is rotationally isolated from its spacer and window holder by the roller bearing assembly.

The second window retention assembly may comprise the second window, its window holder, a second spacer between the second window and its holder, a second sleeve adhered around the second window, the second sleeve in turn be connected to the second spacer via one or more dowel pins, and a second seal assembly hydraulically sealing the second window assembly and constraining fluid being tested to the fluid analysis region. The second window assembly may be employed to set the initial gap or distance between the opposed, substantially flat surfaces of the windows, and aligned the crystal axes of the windows. Importantly, the second window is rotationally connected to its window holder and spacer.

The first polarization filter may be positioned in a holder equipped with a rotary arm, which may be manually operated, or automatically operated via a mechanical or wireless connection, optionally to a logic device, such as a computer. The second polarization filter similarly is held in a holder, and may or may not be equipped with a rotary arm or other component.

Apparatus within this aspect of the invention include those wherein the cell body, window holders, spacers, sleeves, roller bearings, and seal assemblies may comprise the same or different materials selected from metals (for example stainless steel, nickel alloys, and the like), plastics and ceramics. High-pressure tubing fittings for fluid inlet and outlet connections may also comprise one or more of these materials. Tubing fittings and window holders may be connected to the cell body via threaded connections, but this is not a required mode of connection.

The windows may comprise any natural or synthetic material having suitable optical properties (substantially transparent) and mechanical properties able to withstand the desired temperature and pressure conditions. Suitable materials include sapphire and quartz. Certain embodiments of apparatus of the invention may have two or more viewing ports. The light source used, which may be UW, visible, IR, or other electromagnetic source, produces a light beam which enters and passes through one of the polarization filters producing a fully or partially polarized light beam, which then passes through bores through the first window assembly and passes through the fluid sample analysis region. The light continues to pass through the second window assembly and lands upon the second polarization filter. Crystalline material (such as wax) in the fluid sample rotates the plane of polarization of the transmitted polarized light. Therefore if the two polarization filters are misaligned by 90 degrees, only light that passes through a crystalline material in the sample will pass through the second filter (i.e. the polarization plane has been rotated 90 degrees), where a human operator or computer may view the exiting light. Consequently, if the two polarization filters are aligned, light which passes through a crystalline material (such as wax) will not pass through the second filter and therefore will not be viewed by a human operator or computer; however light which passes through or around a non-crystalline material (such as asphaltene) will pass through the second filter, where a human operator or computer may view the exiting light. Using this knowledge, one can distinguish between crystalline and non-crystalline materials that co-exist. Apparatus within the invention may comprise more than one observation port, for example, one or more observation ports positioned generally perpendicular to the longitudinal axis of one or both of the fluid and light paths. One of the viewing ports may allow a camera or other charge couple device to visually access the sample analysis region. Another viewing port may allow light from a second light to enter the sample analysis region. In certain embodiments the viewing port or ports may allow viewing of the sample from the moment the sample begins passing through the sample analysis region until it exits the sample region.

Apparatus within this aspect of the invention include those wherein the seal assemblies may comprise materials selected from mechanical barriers, interfacial barriers and any other form of barrier that would prevent the sample from leaking past the windows. An example of a mechanical barrier may be an elastomeric membrane; an example of an interfacial barrier may be an interface between two immiscible fluids.

Certain embodiments of apparatus of the invention may be described as a high-pressure cross-polar microscopy cell comprising:
(a) a cell body having a fluid flow-through passage and a light passage intersecting the fluid flow-through passage at an adjustable light pathlength fluid analysis region in the cell body;
(b) a first light passage assembly connected to the cell body and comprising a first polarization filter, a first window retention assembly, and a first light-transmissive window, the first window retention assembly comprising a first bore therethrough partially defining the light passage, the first window retention assembly comprising a first window holder and means for rotational decoupling of the first window from the first window holder during adjustment of the light pathlength; and
(c) a second light passage assembly connected to the cell body and comprising a second polarization filter, a second window retention assembly, and a second light-transmissive window, the second window retention assembly comprising a second bore therethrough partially defining the light passage, the second window retention assembly comprising a second window holder and means for allowing rotational coupling of the second window and the second window holder.

In certain embodiments, the means for rotational decoupling of the first window from the first window holder during adjustment of the light pathlength may comprise a first spacer between the first window and the first window holder, a first sleeve adhered to the first window, one or more pins connecting the first sleeve and first spacer, and a roller bearing assembly between the first spacer and the first window holder; and the means for allowing rotational coupling of the second window and the second window holder may comprise a second spacer between the second window and the second window holder, a second sleeve adhered to the second window, and one or more pins connecting the second sleeve and second spacer. While the described means for rotationally coupling and rotationally decoupling are useful in certain embodiments of apparatus of the invention, apparatus and methods of the invention are not limited to these components and their implementation, and other functionally equivalent components and their implementation are considered within the invention.

Another aspect of the invention are methods of observing a sample, one method comprising:
(a) in an apparatus of the invention, setting an initial distance between the opposed, substantially flat surfaces of the windows and aligning crystal axes of the windows;
(b) rotating one or both of the polarization filters so that the filters are cross-polarized;
(c) adjusting the distance between the opposed, substantially flat surfaces of the windows;
(d) rotating the first polarization filter and allowing an amount of polarized light to pass through the first window and the sample analysis region;
(e) flowing a sample to be analyzed into the sample analysis region; and
(f) observing one or more features of the sample while the sample flows through the Sample analysis region.

Methods within this aspect of the invention include those wherein steps (a)-(e) may be carried out in the order listed, or a different order, and step (f) may be carried out during or after step (e). Other methods within the invention include those using the second window holder to accomplish step (c), and using the first window older to accomplish step (d). The process of crossing and uncrossing the polarizers allows crystalline particles to be distinguished from amorphous particles.

These and other features of apparatus and methods of the invention will become more apparent upon review of the detailed description of the invention and the claims that follow.

BRIEF DESCRIPTION OF THE DRAWINGS

The manner in which the objectives of the invention and other desirable characteristics may be obtained is explained in the following description and attached drawing in which.

It is to be noted, however, that the appended drawings are not to scale and illustrate only typical embodiments of this invention, and are therefore not to be considered limiting of its scope, for the invention may admit to other equally effective embodiments.

DETAILED DESCRIPTION

In the following description, numerous details are set forth to provide an understanding of the present invention. However, it will be understood by those skilled in the art that the present invention may be practiced without these details and that numerous variations or modifications from the described embodiments may be possible.

As explained in the Background section, fluids under the influence of changes in one or more of pressure, temperature, fluid mixing, and/or chemical composition, may contain or develop solid particles that are of interest. One method of investigation uses visible light passing through a sample of the fluid to study the development and properties of these solid particles. There are equipment and experimental limitations to increasing the power of the light source, yet some fluid samples transmit less light than others; therefore it is desirable to be able to change the thickness of the fluid sample under investigation. Furthermore it is desirable to make this change while the sample remains at or near the pressure and temperature of interest. One purpose of apparatus and methods of the invention is to provide apparatus for viewing pressurized fluid samples using polarized light and a microscope.

Figure 1:
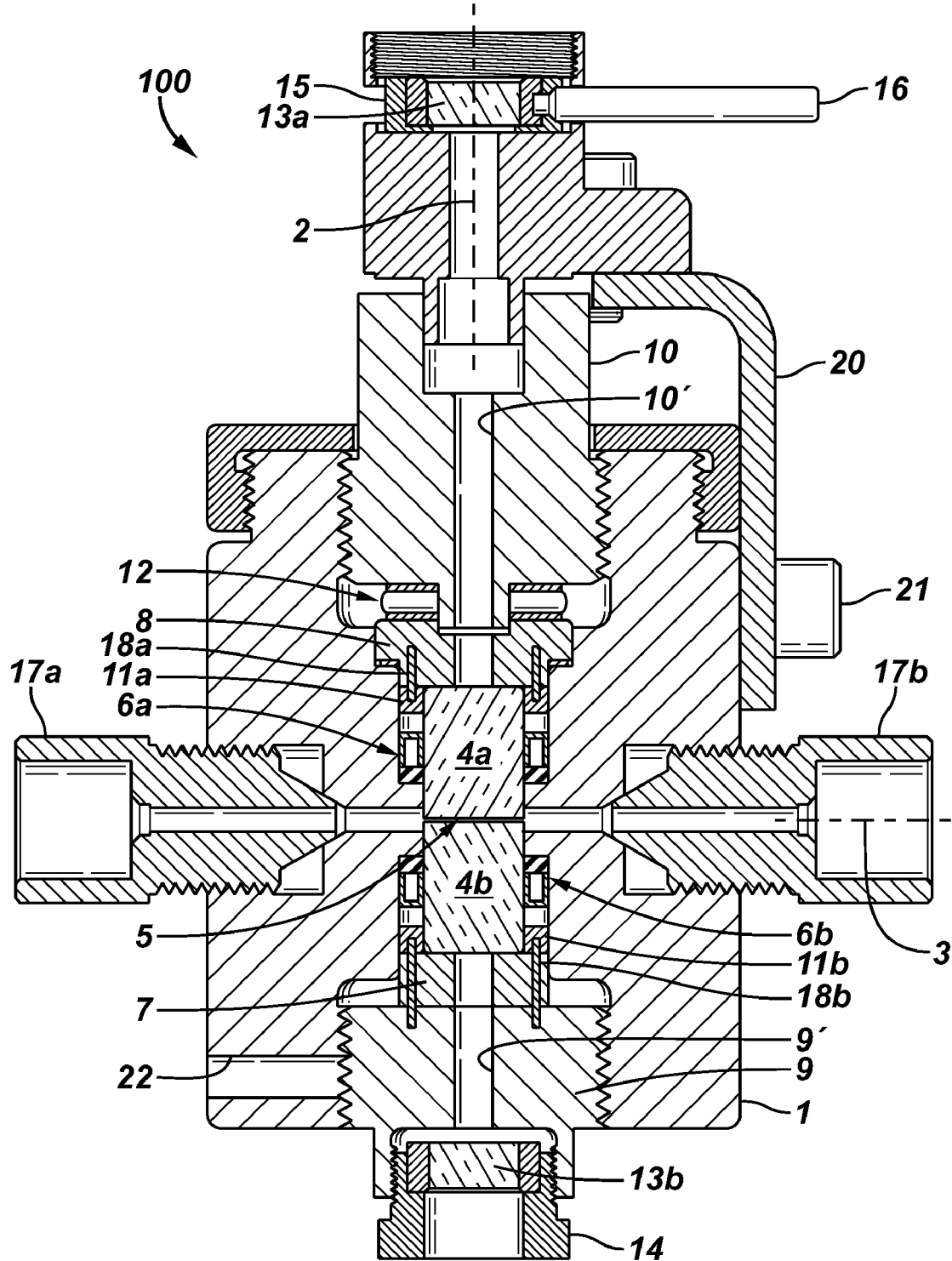
FIG. 1 is a schematic cross-sectional view of an apparatus within the invention.

One embodiment 100 of an apparatus within the invention, sometimes referred to herein as a "high-pressure, cross-polarization microscopy cell, or HPCPM cell, is illustrated in FIG. 1. While embodiment 100 employs a visible light source, this does not preclude the use of other electromagnetic sources. Embodiment 100 comprises cell body 1 made of a high strength material (nickel alloy is one option) comprising window holders 9 and 10 each having internal bores 9' and 10', respectively. Bores 9', 10' form the main portion of an optical path generally along an axis 2 of cell body 1. The optical path intersects a fluid path, which is generally aligned with another axis of the cell body designated at 3, at an adjustable gap 5 between two sapphire windows 4a, 4b. Sapphire windows 4a, 4b are cylindrical in form in embodiment 100 and have their crystal a-axis aligned with their longitudinal axis, although the invention is not limited to cylindrical windows, and other crystal orientations may be used. Surrounding each window is a seal assembly 6a, 6b, that contains the fluid being tested to the region between windows 4a, 4b, and along the fluid path. Windows 4a, 4b are each supported by respective spacers 7 and 8, which are made from hardened stainless steel (or other appropriate material) and lapped to a very high flatness specification. Spacers 7, 8 are restrained by respective window holders 9, 10 which resist the fluid pressure within the cell. Spacer 7 also serves the key role in rotationally coupling window 4b with window holder 9, while spacer 8 serves the key role in rotationally isolating window holder 10 from window 4a. Window holder 9 is rotationally coupled to its spacer 7 and sapphire window 4b in embodiment 100 using a sleeve 11b which is attached using a high temperature adhesive to window 4b and one or more dowel pins 18b through window spacer 7 and into window holder 9. This part rotation is used to set the initial distance of gap 5 within the apparatus and also to align the crystal a-axes of windows 4a, 4b. In contrast, window holder 10 is rotationally isolated from window 4a with the use of a roller bearing assembly 12. In embodiment 100, spacer 8 is indexed to cell body 1 and coupled via one or more dowel pins 18a to sleeve 11a. Other components along the optical path in embodiment 100 include polarizing filters 13a, 13b and polarizing filter holders 14 and 15.

During the set-up for a study using embodiment 100, polarizing filters 13a, 13b are rotated so that their transmittance planes are at 90 degrees to each other. The effect of this "crossed" polarization orientation is to block all the light passing along the optical path. This adjustment is completed using filter holder 14. During the course of fluid studies, polarizing filter 13a is rotated by 90 degrees using a rotary arm 16 to either minimize the light loss or to produce extinguishment of the light passing through the fluid. The polarized light may be used to distinguish between crystalline and non-crystalline particles that appear in the fluid based on the effect that the particles have on polarized light. For example the crystalline structure of wax particles de-polarizes the light. Therefore wax particles may be distinguished from other particles present in the fluid (such as amorphous asphaltenes particles) since wax particles appear as bright spots when the polarizing filters are crossed.

The fluid path along axis 3 may be accessed via high-pressure tube fittings 17a, 17b, one of which are used to inject sample fluid into cell body 1 and into gap 5, sometimes referred to herein as the sample analysis region. Typically the temperature and pressure of the fluid are explicitly controlled as they are often critical experimental variables during the fluid studies. Therefore, fluid inlet tubing may be connected to one or more pressure-controlled pumps, and the entire apparatus located within an environmentally-controlled chamber.

Figure 2:
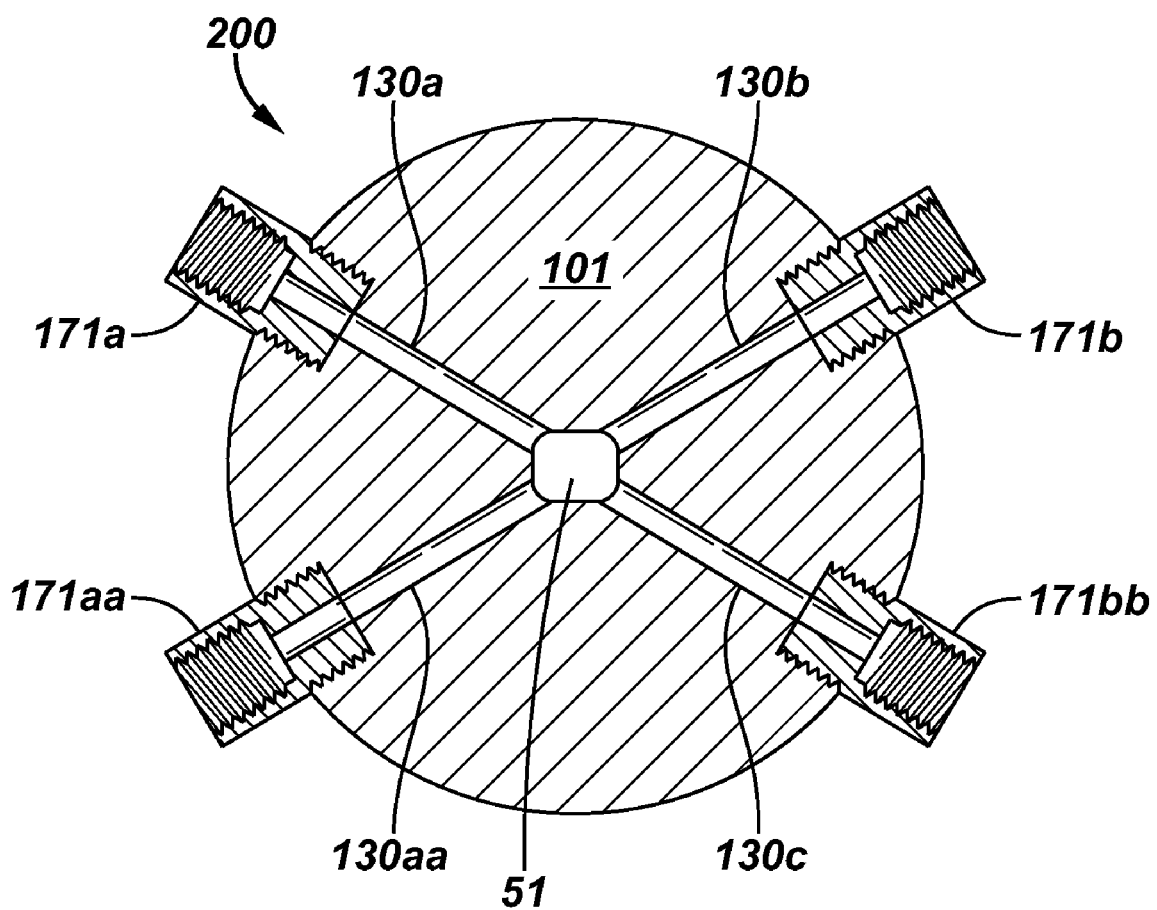
FIG. 2 is a schematic cross-sectional view of a second apparatus within the invention.

FIG. 2 is a schematic cross-sectional view, taken through a plane including fluid flow passages and fluid analysis region, of another apparatus embodiment 200 in accordance with the invention. Embodiment 200 includes two fluid inlets 171a and 171aa, and two fluid outlets 171b and 171bb for added testing flexibility. For example, a fluid sample might traverse through tubing connection 171a, flow channel 130a, fluid analysis region 51, flow channel 130b and/or 130c, depending on the fluids to be tested, desires of the operator, and the like. Connections to fluid pumps and other accessories are not illustrated. Alternatively, fluid sample may enter through inlet 171aa, fluid flow passage 130aa, sample analysis region 51, and exit through flow channel 130b and/or 130c and fluid outlet 171b and/or 171bb, as desired. Suitable valving, not illustrated, would be used to direct fluid sample to the desired paths. This might be beneficial if, for example, an inordinate amount of solids develop in one fluid passage. In those instance the other fluid passages might be used, either as alternative fluid sample passages, or to add solvents for cleaning a blocked fluid passage.

Adjustment capability of gap or fluid analysis region 5 of apparatus of the invention is desirous in fluid studies at least in part because different fluids transmit different levels of light energy. Additionally, since localized fluid heating is experimentally detrimental it is not an option to simply increase the light source intensity. Therefore, varying the gap 5 between windows 4a, 4b during the course of a study adds a new dimension to the analytical capability of apparatus of the invention. The design of apparatus within the invention allows for the thickness of the gap between the windows to be varied while the fluid is pressurized and without affecting the initial alignment of the window crystal axes and the polarizing filters. Rotating the window holder 10 in isolation from the other components adjusts window spacing without affecting any of the other cell parameters.

In certain embodiments, the entire apparatus may be temperature controlled. Sources of temperature control include liquid baths, liquid jackets, pettier devices, convection gas baths, and the like. For example, a convection air bath may be employed to control the temperature in the entire apparatus to within ±1° C., and in certain embodiments within ±0.1° C. If vibration is to be minimized, apparatus of the invention may be isolated from its surrounding to minimize vibration of the apparatus.

In operation of apparatus embodiments of the invention, the sample analysis region will contain a fluid that is subjected to pressure and temperature conditions where either solid particles (e.g. wax or asphaltene) or droplets of a second liquid phase will be formed. An operator will be able to directly observe such micrometer-sized particles using a microscope or other optical device. Sample flow conditions (flow rate, temperature, and pressure) using apparatus and methods of the invention may be automated.

Fluid samples may be gaseous, liquid, supercritical, and any combination thereof, and may contain hydrates. The fluid sample may comprise any sample at sub-ambient, ambient, or above-ambient temperature and pressure, including, but not limited to compositions comprising hydrocarbons (including sour hydrocarbons which may include hydrogen sulfide, mercaptans, and other sulfur-containing compounds), water, organic and/or inorganic solids, and may include (or be subjected to conditions leading to formation of) micelles, macromolecules, globules, resins, asphaltenes, wax crystals, hydrocarbon and aqueous based fluids, drilling muds, frac fluids, reservoir fluids, and the like having multiple phases (solids and liquid). The fluid sample composition may comprise one or more of each phase. The term "reservoir" may include hydrocarbon deposits accessible by one or more wellbores. A "wellbore" includes cased, cased and cemented, or open-hole wellbores, and may be any type of well, including, but not limited to, a producing well, a non-producing well, an experimental well, an exploratory well, and the like. Wellbores may be vertical, horizontal, any angle between vertical and horizontal, diverted or non-diverted, and combinations thereof, for example a vertical well with a non-vertical component. The phrase "high temperature, high pressure" means any temperature and pressure conditions that are above atmospheric pressure and above 20° C.

Embodiments 100 and 200, and other embodiments within the invention may include provisions for temperature control as explained herein. In all embodiments of the invention, a power source powers the light source, and may power a DVD, VCR, monitor or other viewing device.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An apparatus comprising:
   (a) a cell body having a fluid flow-through passage and a light passage intersecting the fluid flow-through passage at an adjustable light pathlength fluid analysis region in the cell body, the cell body comprised of material capable of maintaining temperature and pressure in at least the fluid analysis region at least different than ambient conditions;
   (b) first and second light-transmissive windows in the light passage, each window having at least one crystal axis aligned longitudinally with a longitudinal axis of the window, the windows having opposed, spaced apart, substantially flat surfaces defining the adjustable light pathlength fluid analysis region, the first window having a first window holder and the second window having a second window holder, the first window rotationally isolated from the first window holder, the second window rotationally coupled to the second window holder, the first window holder able to gradually translate the first window and thus adjust the light pathlength; and
   (c) first and second light polarization filters positioned in the light passage.

2. The apparatus of claim 1 wherein the first window is rotationally isolated from the first window holder by a first spacer and a roller bearing assembly between the first spacer and the first window holder.

3. The apparatus of claim 2 wherein the first spacer is rotationally coupled to the first window by a first sleeve adhered to the first window, and one or more pins connecting the first sleeve and first spacer.

4. The apparatus of claim 1 wherein the second window is rotationally coupled to the second window holder by a second sleeve adhered to the second window, a second spacer, and one or more pins connecting the second sleeve, second spacer, and second window holder.

5. The apparatus of claim 1 comprising a first seal assembly surrounding the first window and a second seal surrounding the second window, the first and second seals constraining fluid being tested to the fluid analysis region defined between the opposed, spaced apart, substantially flat surfaces of the first and second windows.

6. The apparatus of claim 1 wherein the first window holder is connected to the cell body via a threaded fitting, allowing the first window holder to rotate and gradually translate the first window closer to or further away from the second window, thereby adjusting the distance between the opposed, substantially flat surfaces of the first and second windows, and therefore adjust the size of the fluid analysis region, and thus adjust the light pathlength.

7. The apparatus of claim 1 wherein the first polarization filter is between a light entrance and the first window holder and held in a holder equipped with a rotary arm, and the second polarization filter is positioned in the light passage between a light exit and the second window holder and held in a separate holder which is equipped with a rotary arm.

8. The apparatus of claim 7 wherein the rotary arms are selected from a manually operated rotary arm and an automatically operated rotary arm.

9. The apparatus of claim 1 wherein the cell body and first and second window holders comprise the same or different materials selected from metals, plastics, ceramics, and combinations thereof.

10. The apparatus of claim 1 wherein the first and second windows comprise materials selected from natural and synthetic materials having suitable optical and mechanical properties able to withstand desired temperature and pressure conditions.

11. The apparatus of claim 10 wherein the first and second windows comprise materials selected from sapphire and quartz.

12. The apparatus of claim 1 comprising two or more viewing ports.

13. The apparatus of claim 1 comprising a light source, wherein the light source is selected from UV, visible, IR, or other electromagnetic source.

14. The apparatus of claim 13 wherein the light source produces a light beam which enters and passes through the first polarization filter producing a fully or partially polarized light beam, the fully or partially polarized light beam then passing through a first bore through the first window holder and into the fluid sample analysis region, wherein depending on the sample contents, portions of the polarized light may be depolarized, and depolarized light exits the sample analysis region through the second window, a bore through the second window holder, and through the second polarization filter, where a human operator or computer may view light exiting the second polarization filter.

15. A high-pressure cross-polar microscopy cell comprising:
  (a) a cell body having a fluid flow-through passage and a light passage intersecting the fluid flow-through passage at an adjustable light pathlength fluid analysis region in the cell body;
  (b) a first light passage assembly connected to the cell body and comprising a first polarization filter, a first window retention assembly, and a first light-transmissive window, the first window retention assembly comprising a first bore therethrough partially defining the light passage, the first window retention assembly comprising a first window holder and means for rotational decoupling of the first window from the first window holder during adjustment of the light pathlength; and
  (c) a second light passage assembly connected to the cell body and comprising a second polarization filter, a second window retention assembly, and a second light-transmissive window, the second window retention assembly comprising a second bore therethrough partially defining the light passage, the second window retention assembly comprising a second window holder and means for allowing rotational coupling of the second window and the second window holder.

16. The apparatus of claim 15 wherein the means for rotational decoupling of the first window from the first window holder during adjustment of the light pathlength comprises a first spacer between the first window and the first window holder, a first sleeve adhered to the first window, one or more pins connecting the first sleeve and first spacer, and a roller bearing assembly between the first spacer and the first window holder.

17. The apparatus of claim 16 wherein the means for allowing rotational coupling of the second window and the second window holder comprises a second spacer between the second window and the second window holder, a second sleeve adhered to the second window, and one or more pins connecting the second sleeve and second spacer.

18. A method comprising:
  (a) in an apparatus comprising a test cell having a cell body, the cell body comprising a fluid flow-through passage and a light passage intersecting the fluid flow-through passage at an adjustable light pathlength fluid analysis region in the cell body, first and second light-transmissive windows in the light passage, each window having a crystal axis aligned longitudinally with a longitudinal axis of the window, the windows having opposed, spaced apart, substantially flat surfaces defining the adjustable light pathlength fluid analysis region, setting an initial distance between the opposed, substantially flat surfaces of the windows and aligning crystal axes of the windows;
  (b) rotating one or both of the polarization filters so that the filters are cross-polarized;
  (c) adjusting the distance between the opposed, substantially flat surfaces of the windows;
  (d) rotating the first polarization filter and allowing an amount of polarized light to pass through the first window and the sample analysis region;
  (e) flowing a sample to be analyzed into the sample analysis region; and
  (f) observing one or more features of the sample.

19. The method of claim 18 comprising carrying out steps (a), (b), (c), (d), and (e) in sequential order, and carrying out step (f) during step (e).

20. The method of claim 18 comprising using the second window holder to accomplish step (c), and using the first window older to accomplish step (d).

* * * * *